US008265763B2

(12) United States Patent
Fahey

(10) Patent No.: US 8,265,763 B2
(45) Date of Patent: Sep. 11, 2012

(54) DEVICE, SYSTEM, AND METHOD TO IMPROVE POWERED MUSCLE STIMULATION PERFORMANCE IN THE PRESENCE OF TISSUE EDEMA

(75) Inventor: Brian Fahey, Palo Alto, CA (US)

(73) Assignee: Niveus Medical, Inc., Palo Alto, CA (US)

( * ) Notice: Subject to any disclaimer, the term of this patent is extended or adjusted under 35 U.S.C. 154(b) by 536 days.

(21) Appl. No.: 12/548,155

(22) Filed: Aug. 26, 2009

(65) Prior Publication Data

US 2010/0057149 A1 Mar. 4, 2010

Related U.S. Application Data

(60) Provisional application No. 61/190,108, filed on Aug. 26, 2008, provisional application No. 61/201,877, filed on Dec. 15, 2008.

(51) Int. Cl.
*A61N 1/00* (2006.01)
(52) U.S. Cl. .......................................................... 607/48
(58) Field of Classification Search ...................... 607/48
See application file for complete search history.

(56) References Cited

U.S. PATENT DOCUMENTS

| 4,390,023 | A | 6/1983 | Rise |
| 4,480,830 | A | 11/1984 | Petrofsky et al. |
| 4,580,569 | A | 4/1986 | Petrofsky |
| 4,619,266 | A | 10/1986 | Hodgson |
| 4,736,752 | A | 4/1988 | Munck et al. |
| 4,805,636 | A | 2/1989 | Barry et al. |
| 4,811,742 | A | 3/1989 | Hassel et al. |
| 4,838,272 | A | 6/1989 | Lieber |
| 4,867,166 | A | 9/1989 | Axelgaard et al. |
| 4,969,468 | A | 11/1990 | Byers et al. |
| 5,010,896 | A | 4/1991 | Westbrook |
| 5,016,635 | A | 5/1991 | Graupe |
| 5,070,873 | A | 12/1991 | Graupe et al. |
| 5,097,828 | A | 3/1992 | Deutsch |
| 5,314,423 | A | 5/1994 | Seney |
| 5,336,255 | A | 8/1994 | Kanare et al. |
| 5,397,338 | A | 3/1995 | Grey et al. |
| 5,507,788 | A | 4/1996 | Lieber |
| 5,549,656 | A | 8/1996 | Reiss |
| 5,674,262 | A * | 10/1997 | Tumey ............................ 607/48 |

(Continued)

FOREIGN PATENT DOCUMENTS

JP 2001-025510 1/2001

(Continued)

OTHER PUBLICATIONS

Lacey et al.; Reductions in the amount of time spent in direct patient care by staff nurses in North Carolina; North Carolina Center for Nursing; Aug. 2002.

(Continued)

*Primary Examiner* — George Manuel
(74) *Attorney, Agent, or Firm* — Shay Glenn LLP

(57) ABSTRACT

The invention provides systems and methods for neuromuscular electrical stimulation to muscle tissue. Stimulation electrodes may be provided on a stimulation pad, configured to provide electrical stimulation to a target tissue. A system for neuromuscular electrical stimulation may also include pressure generating mechanisms that may provide a compressive force to a region with the target tissue, thereby removing some excess third space fluid from the region.

37 Claims, 12 Drawing Sheets

U.S. PATENT DOCUMENTS

| | | | |
|---|---|---|---|
| 5,702,323 | A | 12/1997 | Poulton |
| 5,702,429 | A | 12/1997 | King |
| 6,266,558 | B1 | 7/2001 | Gozani et al. |
| 6,301,500 | B1 | 10/2001 | Van Herk et al. |
| 6,324,432 | B1 | 11/2001 | Rigaux et al. |
| 6,341,237 | B1 | 1/2002 | Hurtado |
| 6,480,731 | B1 | 11/2002 | DeLuca et al. |
| 6,505,078 | B1 | 1/2003 | King et al. |
| 6,567,696 | B2 | 5/2003 | Voznesensky et al. |
| 6,829,510 | B2 | 12/2004 | Nathan et al. |
| 6,840,955 | B2 | 1/2005 | Ein |
| 6,944,503 | B2 | 9/2005 | Crowe et al. |
| 7,146,220 | B2 | 12/2006 | Dar et al. |
| 7,172,564 | B2 | 2/2007 | Bosco |
| 7,204,832 | B2 | 4/2007 | Altshuler et al. |
| 7,221,980 | B2 | 5/2007 | Kotlik et al. |
| 7,236,832 | B2 | 6/2007 | Hemmerling et al. |
| 7,257,448 | B2 | 8/2007 | Crowe et al. |
| 7,276,058 | B2 | 10/2007 | Altshuler et al. |
| 7,473,251 | B2 | 1/2009 | Knowlton et al. |
| 7,483,738 | B2 | 1/2009 | Tamarkin et al. |
| 7,499,746 | B2 | 3/2009 | Buhlmann et al. |
| 2002/0143365 | A1 | 10/2002 | Herbst |
| 2002/0151951 | A1 | 10/2002 | Axelgaard et al. |
| 2004/0044384 | A1 | 3/2004 | Leber et al. |
| 2004/0254624 | A1 | 12/2004 | Johnson |
| 2005/0288730 | A1 | 12/2005 | Deem et al. |
| 2006/0142816 | A1 | 6/2006 | Fruitman et al. |
| 2007/0106343 | A1 | 5/2007 | Monogue et al. |
| 2007/0203435 | A1 | 8/2007 | Novak |
| 2008/0161883 | A1 | 7/2008 | Conor |
| 2010/0004715 | A1 | 1/2010 | Fahey |
| 2011/0082517 | A1* | 4/2011 | Brezel et al. ................... 607/48 |

FOREIGN PATENT DOCUMENTS

| | | |
|---|---|---|
| JP | 2002-052000 | 2/2002 |
| KR | 10-866543 B | 11/2008 |
| WO | WO 01/52759 A1 | 7/2001 |
| WO | WO 03/086217 A1 | 10/2003 |
| WO | WO 2004/089185 A2 | 10/2004 |
| WO | WO 2004/098703 A2 | 11/2004 |
| WO | WO 2005/075018 A1 | 8/2005 |
| WO | WO 2005/105203 A1 | 11/2005 |
| WO | WO 2007/017778 A2 | 2/2007 |
| WO | WO 2007/041540 A1 | 4/2007 |
| WO | WO 2007/046886 A1 | 4/2007 |
| WO | WO 2008/032282 A2 | 3/2008 |
| WO | WO 2008/034607 A1 | 3/2008 |
| WO | WO 2008/075250 A1 | 6/2008 |
| WO | WO 2009/009661 A1 | 1/2009 |

OTHER PUBLICATIONS

Miklavcic et al.; Electrical Properties of Tissues; Wiley Encyclopedia of Biomedical Engineering; 2006.

Morris, Peter E.; Moving our critically ill patients: mobility barriers and benefits; Critical Care Clinics; vol. 23; pp. 1-20; 2007.

Prausnitz, Mark R.; The effects of electrical current applied to skin: a review for transdermal drug delivery; Advanced Drug Delivery Reviews; vol. 18; pp. 395-425; 2006.

Rafolt et al.; Dynamic force responses in electrically stimulated triceps surae muscles: effects of fatigue and temperature; Artificial Organs; vol. 23; No. 5; pp. 436-439; 1999.

Solomon et al.; The effects of TENS, heat, and cold on the pain thresholds induced by mechanical pressure in healthy volunteers; Neuromodulation; vol. 6; No. 2; pp. 102-107; 2003.

Stecker et al.; Mechanisms of electrode induced injury. Part 1: theory; Am. J. End Tech.; vol. 46; pp. 315-342; 2006.

Suganuma et al.; Measurement of tension of tendon tissue based on electrical impedance; J. Ortho Science; vol. 9; pp. 302-309; 2004.

Zanotti et al.; Peripheral muscle strength training in bed-bound patients with COPD receiving mechanical ventilation: effect of electrical stimulation; Chest; vol. 124; No. 1; pp. 292-296; Jul. 2003.

Fahey, Brian J.; U.S. Appl. No. 12/710,243 entitled "Systems and Methods of Powered Muscle Stimulation Using an Energy Guidance Field," filed Feb. 22, 2010.

Fahey, Brian J.; U.S. Appl. No. 12/943,486 entitled "Synergistic Muscle Activation Device," filed Nov. 10, 2010.

Baker et al.; Effects of waveform on comfort during neuromuscular electrical stimulation; Clin Ortho Res; vol. 233; pp. 75-85; 1988.

Bennie et al.; Toward the optimal waveform for electrical stimulation of human muscle; Eur J Appl Physiol; vol. 88; pp. 13-19; 2002.

Lyons et al.; An investigation of the effect of electrode size and electrode location on comfort during stimulation of the gastrocnemius muscle; Medical Engineering & Physics; vol. 26; pp. 873-878; 2004.

Petrofsky et al.; Estimation of the distribution of intramuscular current during electrical stimulation of the quadriceps muscle; Eur J Appl Physiol; vol. 103(3); pp. 265-273; Jun. 2008.

* cited by examiner

DEVICE, SYSTEM, AND METHOD TO IMPROVE POWERED MUSCLE STIMULATION PERFORMANCE IN THE PRESENCE OF TISSUE EDEMA

CROSS-REFERENCE

This application claims the benefit of U.S. Provisional Application No. 61/190,108, filed Aug. 26, 2008; and U.S. Provisional Application No. 61/201,877, filed Dec. 15, 2008; which applications are incorporated herein by reference in their entirety.

BACKGROUND OF THE INVENTION

Neuromuscular electrical stimulation (NMES) (also referred to as powered muscle stimulation, functional muscle stimulation, electrical muscle stimulation, and other terms) is an established technology with many therapeutic uses, including pain relief, prevention or retardation of disuse atrophy, and improvement of local blood circulation. NMES is typically delivered as an intermittent and repeating series of short electrical pulses. In many implementations, these pulses are delivered transcutaneously by surface electrodes that are attached to a person's skin. Electrodes may be held to the skin through the use of straps, adhesives, or other mechanisms, and often contain a coupling layer composed of gel or other materials that is capable of enhancing the efficiency of energy transfer from the electrode to the skin and underlying tissues.

A group of persons who could potentially show large benefit from NMES therapy are those who are immobilized or confined to bed rest. Periods of immobilization lead to muscle atrophy and weakness, and have severe effects on a person's physical capacity. Following immobilization, a previously active and functional person will typically require extensive physical therapy to reclaim their prior level of functionality. NMES may help these persons by preventing or retarding muscle atrophy during immobilization.

Critically ill medical patients comprise a subgroup of the immobilized persons described above. While virtually all of these patients are confined to bed rest, many are also suffering from conditions such as coma or are receiving interventions (such as mechanical ventilation) that generally require sedation and/or analgesia. These sedated or comatose patients are at the highest risk for muscle atrophy because even simple voluntary movements (such as shifting arms/legs in bed or moving one's feet) are often not performed. Consequently, critically ill patients face long paths to recovery that are generally measured in months as opposed to days or weeks.

As part of care for their acute illness, many critically ill patients receive I/V fluids, antibiotics, and other interventions. One common side effect of these medical treatments in immobilized patients is the development of tissue edema. Generally speaking, tissue edema occurs as body fluids accumulate in 'the third space', or the region outside of both cells and vessels. Edema is often caused by microvasculature leakage, and typically results in tissue swelling. This swelling has been known affect the ability of NMES to induce muscle contractions using surface electrodes placed on the skin. Increased electrical impedance and increased distance between surface electrodes and underlying muscles are factors that contribute to this problem. Although previous work in the medical literature has noted that certain types of electrical stimulation may prevent the onset of local edema after traumatic injury, these types of therapies have not been conclusively shown to prevent or reduce widespread edema.

Existing NMES devices do not have features or compensation mechanisms to address tissue edema. Because of this, these devices provide highly variable performance in and are of limited utility amongst patients suffering from this condition. For example, with existing NMES devices many patients in this group will require the delivery of much higher than average energy levels in order to transcutaneously stimulate muscle tissues. Performance variability increases labor costs associated with the delivery of NMES, and the requirement of using enlarged energy levels increases the potential for burns, muscle damage, and other adverse events. These factors and others limit the application of NMES therapy to edematous patients and to immobilized critically ill patients as a whole, a group that could benefit significantly from the therapy.

Therefore, a need exists for the delivery of safe and effective NMES therapy to immobilized critically ill patients, which could be facilitated by a device, system, and method designed to minimize the effects of tissue edema on NMES. Such a device, system, and method could allow for a larger patient cohort to receive the beneficial effects of a well established medical therapy.

SUMMARY OF THE INVENTION

The invention provides systems and methods for neuromuscular electrical stimulation to muscle and/or nervous tissue. Various aspects of the invention described herein may be applied to any of the particular applications set forth below or for any other types of electrical stimulation and sensing systems or methods, or for any applications to subjects with edematous tissue. The invention may be applied as a standalone system or method, or as part of an integrated medical treatment system. It shall be understood that different aspects of the invention can be appreciated individually, collectively, or in combination with each other.

Detailed within are a device, system, and method for improving neuromuscular electrical stimulation (NMES) performance in persons with tissue edema. Use of the device, system, and method may permit near-normal or improved operation of an NMES device in an edematous person, allowing for reliably successful transcutaneous stimulation of muscle tissue without the need for excessively high energy amplitude. The device, system, and method will enable a greater percentage of immobilized and/or critically ill persons to receive successful NMES. By reducing inter-person variability and associated labor costs, the device, system, and method will also enable more widespread adoption of NMES therapy in critical care and other settings.

The system may include two major components: a specialized electrical stimulation pad and a control unit that contains microprocessor or other control elements that can generate a waveform/signal for NMES therapy. The control unit may also contain electronics that can execute safety and/or optimization protocols. The specialized pad may be adapted to apply pressure or mild squeezing force to tissue, temporarily moving excess third space fluid away from the site of desired muscle stimulation. Additionally, the pad may contain two or more stimulation electrodes and potentially other elements related to the safety and optimization of NMES therapy. Connecting the pad and the control unit are a means for transmitting and receiving electrical signals, such as NMES waveforms. The connection means could be a standard cable connection, a wireless connection such as Blue-tooth, WiFi, infrared, or other similar connections.

The device and system are useful because when implemented they will enable effective NMES therapy in a subset of persons where NMES has been shown to be ineffective, inconsistent, and difficult to implement. For example, it is known that critically ill patients often suffer tremendously from disuse atrophy and ICU-related muscle weakness (see Morris, *Crit Care Clin* 23 (2007) pp. 1-20, incorporated herein by reference). It is also known that NMES can prevent disuse atrophy and preserve muscle strength in immobilized persons. Despite this, NMES has not found widespread use in critical care treatment facilities in the U.S. A large portion of the problem is that many of these patients suffer from tissue edema, and existing NMES devices do not have compensation mechanisms to account for this condition. By providing these compensation mechanisms, the device and system described herein will make NMES therapy more consistently successful, more predictable, and importantly, easier to deliver to critical ill patients as a whole. The method described herein is useful because it enables successful and straightforward use of the device and system described herein. Thus, the device, system, and method described herein may allow for a greater number of persons to receive the benefits of NMES therapy.

The presently described device, system, and method have a number of benefits, including: 1) They allow for improvements in medical patient care, 2) They improve the performance of an existing medical therapy in a large number of patients, 3) They will enable a new group of patients who typically do not benefit from NMES-based muscle atrophy treatment to receive efficacious therapy, and 4) They will provide inter-patient consistency and simplify NMES treatment in patients with tissue edema, reducing the workload of a medical care provider.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Figure 1:
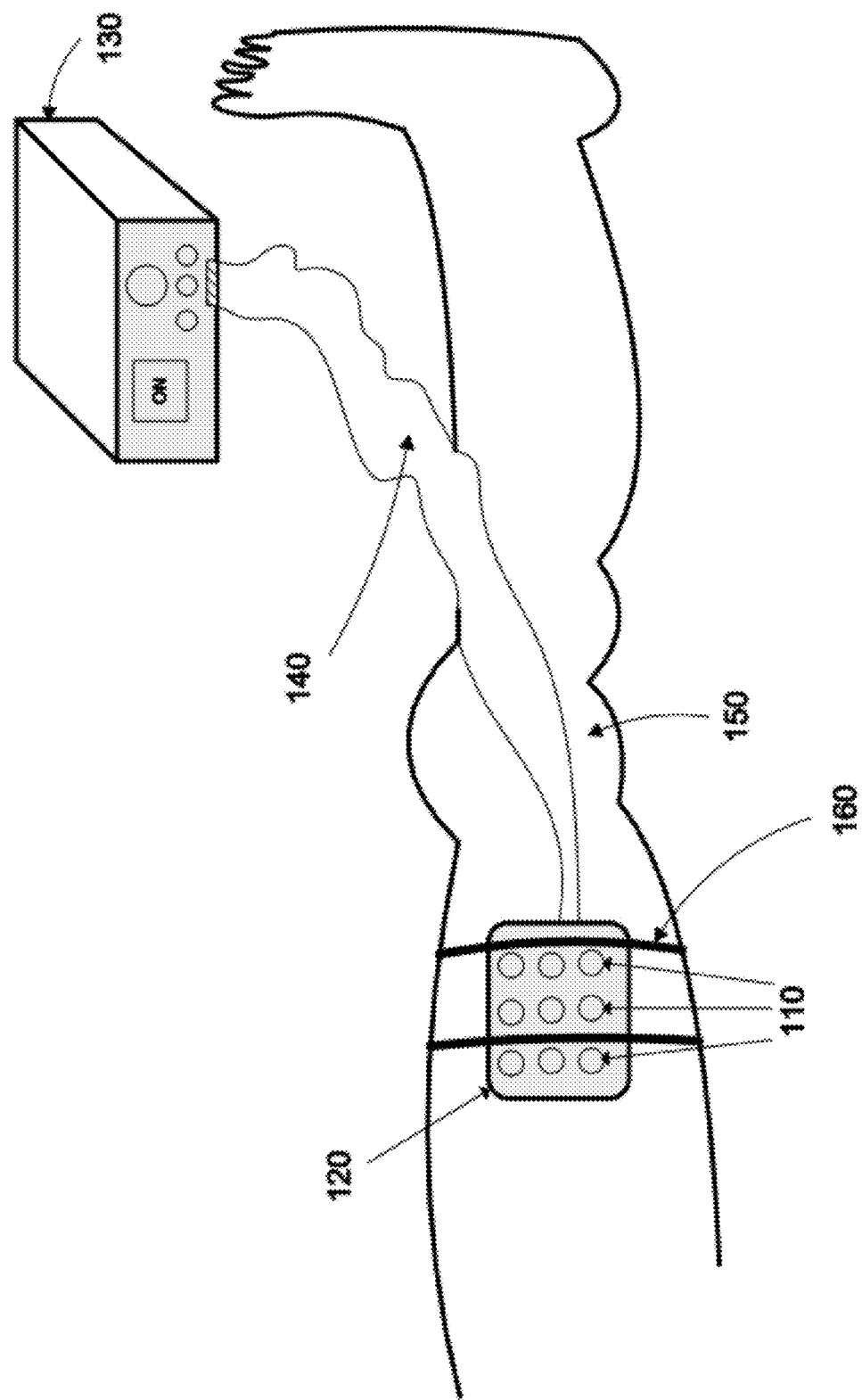
FIG. 1 provides an overview of a neuromuscular electrical stimulation (NMES) device and system.

FIG. 1 provides an overview of a neuromuscular electrical stimulation (NMES) device and system. The NMES system may include one or more electrodes 110 placed within a thin, flexible housing 120. A control unit 130 may be electrically connected to the one or more stimulating electrode. In some embodiments, the NMES may also include or more sensing electrodes placed within the thin, flexible housing, and the control unit may communicate with the one or more sensing electrode. The control unit may communicate with the electrodes through a series of wire connections. The wired connections may be formed into a connection cable 140. The system may be used for neuromuscular electrical stimulation (NMES) of muscle and/or nervous tissue.

A stimulation assembly may include one or more stimulating electrode 110. In some embodiments, the stimulation assembly may be a stimulation pad comprising one or more electrodes placed within a thin, flexible housing 120. In a preferable embodiment of the invention, the thin, flexible housing may form a substrate or support for an electrode pad. The thin flexible housing may be formed of a material that may enable the pad to conform to an anatomical placement on a subject. For example, the housing may include a deformable or elastic component. The placement of the pad may determine which muscle and/or nervous tissue of the subject may be stimulated by the NMES device. For instance, the muscle tissue proximate to the pad may be stimulated.

The one or more stimulating electrode 110 may be mechanically attached or integrated into the substrate 120. A stimulating electrode may be configured to provide electrical stimulation to a target muscle and/or nervous tissue. The stimulation assembly may be configured such that the one or more electrodes may have any relative position. In a preferable embodiment, an array of stimulating electrodes may be provided on the pad. Any number of electrodes may be provided on the array. For example, an array may be formed of n rows and m columns, where n and m are any integer with a value of one, two, three, four, five, six, seven, eight, nine, ten, or greater. In other embodiments, the array of stimulating electrodes need not be arranged into rows and columns and may have any placement on a pad. For instance, the stimulation electrodes may alternatively form one or more circles, lines, or any other geometric arrangement. A stimulation electrode may be configured to provide electrical stimulation to a target muscle and/or nervous tissue.

The stimulation assembly may be in contact with a body part of a subject 150. For example, the stimulation assembly may be placed on the skin of a subject. The subject may be a patient, such as a comatose, sedated, analgesed patient, or a patient at the ICU, or may be a clinical test subject, or any other human, mammal, or any other animal that may receive NMES. In some embodiments, the subject may have edematous tissue. In some instances, the subject may have excess adipose tissue or be overweight or obese. The stimulation assembly may be held in place against the body part of the subject. Stimulation electrodes may be built into the pad in such a way that they make good electric contact with the skin and that they are electrically isolated from each other. One or more stimulation electrodes of the stimulation assembly may provide electrical stimulation to underlying target muscle and/or nervous tissue of the subject. In some instances, a stimulation electrode may contact a subject in a location proximate to the target tissue. The stimulation electrode may be in electrical communication with the target tissue. The stimulating electrodes may be in electrical contact with the underlying target tissue, even if they are not in direct physical contact with the tissue. Thus, the stimulating electrodes may be able to electrically communicate with target tissue transdermally. The target tissue of the subject may or may not be edematous.

The stimulation assembly may be held in place by any sort of attachment mechanism. See, e.g., U.S. Pat. No. 6,829,510; U.S. Pat. No. 7,146,220; U.S. Pat. No. 6,341,237, which are hereby incorporated by reference in their entirety. For example, a strap-based attachment mechanism 160 may be used (perhaps in combination with an adhesive) to hold the stimulation assembly (e.g., such as a stimulation pad) onto the body part receiving NMES. The strap-based attachment mechanism may include one, two, three, or more straps. The straps may circumscribe a body part of the subject. The strap may be used to apply static pressure to the stimulation region. The strap may be applying compressive force of a sufficient pressure to remove excess third space fluid. In some instances, the pressure may be sufficient to remove at least some of the excess third space fluid, while in other embodiments, the pressure may be sufficient to remove most or substantially all of the excess third space fluid.

One example of a pressure range being applied may include 2-20 lbs for the area covered by the pressure assembly. The pressure assembly may cover any amount of area, e.g., approximately on the order of 1 square inch, 4 square inches, 6 square inches, 8 square inches, 10 square inches, 12 square inches, 15 square inches, 25 square inches, etc. In some embodiments, the pressure range may fall near 0.05 psi, 0.1 psi, 0.5 psi, 1 psi, 2 psi, 3 psi, 5 psi, 7 psi, 10 psi, 12 psi, 15 psi, 20 psi, 30 psi, or any pressure therebetween, thereabouts, or greater. In some embodiments, the amount of pressure to remove some third space fluid may be greater than a pressure required to simply maintain electrode contact with a skin surface. Thus, an assembly that may provide the requisite amount of pressure may be a tissue fluid displacing pressure assembly. In some embodiments, the pressure assembly may be in contact with the stimulation assembly, or may or may not be integrally connected to the stimulation assembly.

In some embodiments, a substrate of the stimulation assembly, such as a flexible membrane of a stimulation pad may include an adhesive backing that allows it to retain contact with the person receiving NMES. Alternate (or in some cases, additional) securement mechanisms, such as straps, hooks, other fasteners (such as Velcro, or any other fabric hook-and-loop fastener), elastics, weights, or other mechanisms, may be used instead of an adhesive backing to retain contact with the skin surface and to reduce local tissue edema.

In accordance with an embodiment of the invention, a stimulation pad may contain two or more stimulation electrodes and other element(s) useful for safety and optimization of NMES therapy.

A control unit contains pulse generation electronics as well as both digital and/or analog signal processing components. In accordance with one embodiment shown, the control unit communicates with the electrode array through a series of wire connections. The wire connections may be provided in a connection cable. The control unit may provide electrical stimulation signals to a stimulation electrode. The control unit may also communicate with the stimulation pad through any other wired or wireless connection, radiofrequency transmission, optical, acoustic, or electromagnetic signals, or another suitable mechanism. In the preferred embodiment, the control unit is a separate unit that may be located some distance from the person receiving NMES therapy. In an alternate embodiment, the control unit may be integrated into a housing unit containing the stimulating pad and associated electronics.

In a preferable embodiment, the control unit may contain components such as a signal generator, memory, processor, and power supply. When activated, the control unit may generate electrical stimulation signals that may be transmitted to the stimulation pad, which may couple the energy into the body to activate muscles. In some variations of this embodiment, parameters that describe the electrical stimulation signals transmitted to the pad, such as the amplitude of stimulus, the shape of stimulus waveform, the duration of stimulus signal, and the stimulus signal frequency, may be adjusted by the user or by another mechanism (such as automatic adjustment/optimization).

In some embodiments, one or more sensing electrode may also be provided in a stimulation assembly. The sensing electrode may be configured to provide a feedback signal indicative of a parameter related to a target muscle and/or nervous tissue. A sensor may also provide any other feedback information. For example, sensors may provide information about temperature, force, pressure, movement, etc. The one or more sensing electrode may have any placement on the stimulation assembly. In some instances, the placement of the sensing electrode may be selected relative to the placement of the one or more stimulation electrodes. In some instances, the one or more sensing elements may be contained within the substrate or thin flexible housing. The control unit may also communicate with the one or more sensing electrodes. In some embodiments, the signals provided to the stimulation electrode may depend on signals received from the sensing electrode. Thus, the system may provide a feedback, to control the electrical stimulation provided. The sensors can also be utilized for safety and optimization reasons, and associated circuitry (if applicable) that produce an electronic signal output that is reflective of NMES and electrode characteristics.

In some embodiments, each of the stimulation electrodes may be individually controllable by the control unit. For example, the stimulation electrodes may be connected to the control unit in such a way that for each stimulation electrode, whether any stimulation is provided, the level of stimulation provided, or pulse width, duration, frequency, amplitude, waveform, or any other characteristic of the stimulation provided to the stimulation electrode may be individually controlled by the control box. Thus, customization and localization of stimulation may be closely controlled. See, e.g., PCT Publication No. WO 2007/017778 and PCT Publication No. WO 2005/075018, which are hereby incorporated by reference in their entirety.

There may be a number of parameters that describe the stimulation electrical pulses. These may include voltage amplitude, current amplitude, waveform shape (e.g., square, sinusoidal, exponential, monophasic/biphasic, symmetric/asymmetric), pulse length, pulse repetition frequency, and the relative on/off times between repeating series of pulses. Depending on the mode of operation (e.g., constant current vs. constant voltage stimulation), some of these parameters may be independently user-controlled, while others are dependent on external factors such as the electrical impedance between electrodes.

In some embodiments, the control unit has one or more electrical channels to receive signals originating from sensing elements in the stimulation pad. Upon receiving these signals, the control unit has a means to process these data, evaluate received data, and make output adjustments. This evaluation is performed by an embedded microprocessor with associated software and/or firmware, an application specific integrated circuit, a field programmable gate array, a comparative means (ex. comparator with or without hysteresis), or other means that will be apparent to those skilled in the art.

Figure 2:
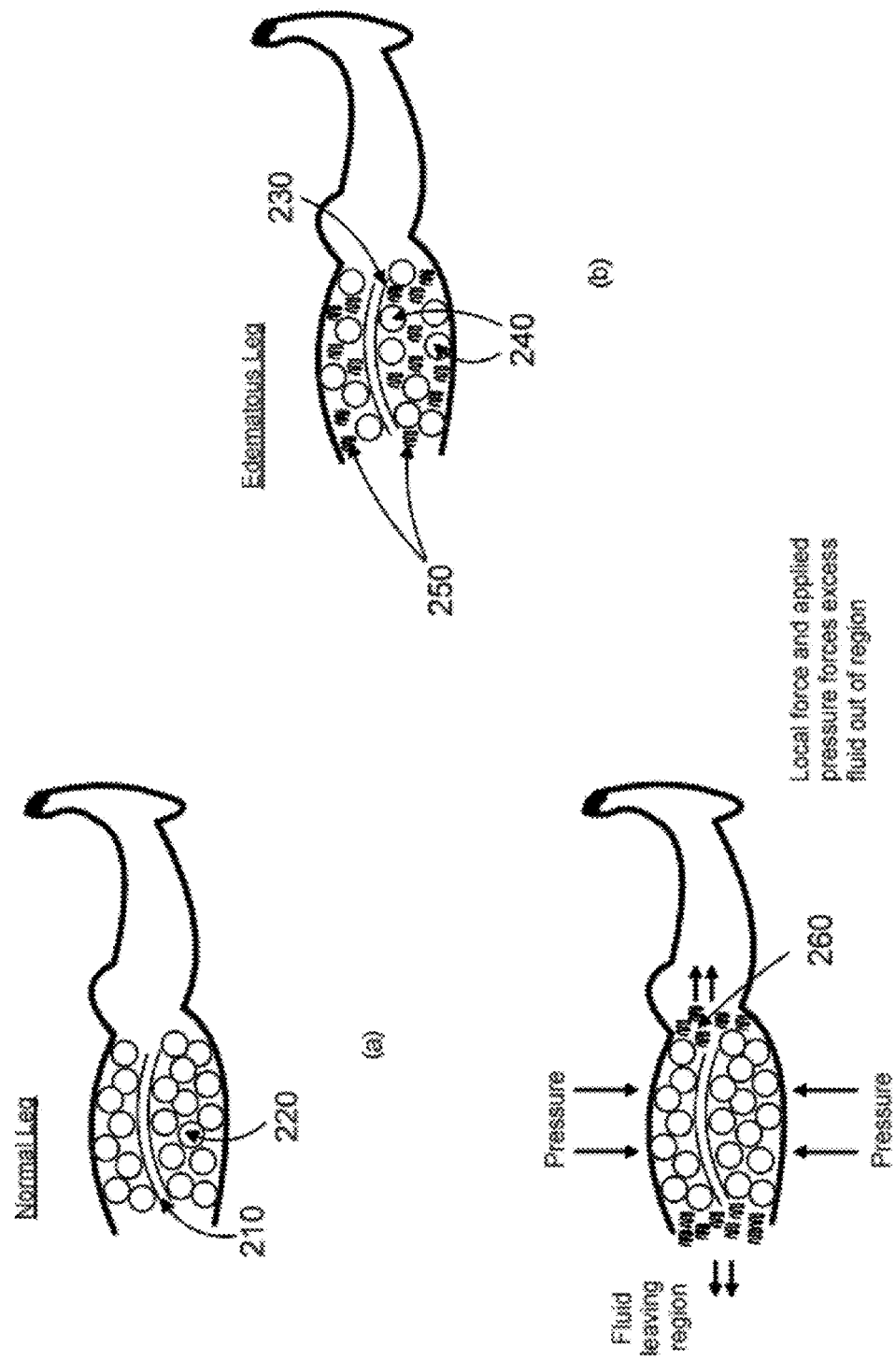
FIGS. 2(*a*)-(*c*) provides an examples of a theory behind an NMES device and system that may provide pressure to a region of a subject's body.

FIG. 2 provides an example of a theory behind an NMES device, system, or method that may provide pressure to a region of a subject's body. FIG. 2(a) shows a normal leg without edema. A leg may include vasculature 210 as well as cells 220 in tissues. FIG. 2(b) shows a leg with fluid accumulation in the third space and the associated swelling. In one example, the leg may include vasculature 230 and cells 240 in tissues, as well as excess extravascular and/or extracellular fluid 250, which may cause swelling in the leg. This may illustrate an edematous or partially edematous leg.

FIG. 2(c) shows a local pressure being applied to edematous tissue, creating a pressure gradient that forces excess third space fluid 260 out of the region. The local pressure may be a compressive force which may be directed substantially perpendicular to the surface of the body part. For example, on a leg, the pressure may be directed inward toward an axis extending along the length of the leg. The compressive force may cause a squeezing in the leg, which may cause at least some of the excess third space fluid to leave the local region that is being squeezed. In various embodiments, depending on the amount and placement of pressure provided, some, most or substantially all of the excess fluid may leave the region receiving the pressure. The excess fluid may leave the region receiving the fluid temporarily or relatively permanently. For example, when the pressure is removed, the excess fluid may immediately or gradually return to the region. Alternatively, the excess fluid may not return to the region, or may return after a long period of time.

There are multiple potential variations of the preferred embodiment. A number of these variations are described in detail below. It will be apparent to those skilled in the art that there are additional variations and embodiments that are not explicitly described in this document. The variations may function on a principle that muscle stimulation with NMES will be more effective and more reliable if tissue edema were locally reduced in the region of desired stimulation. Without being bound by any theory, it may be postulated that removing excess third space fluid from a localized region may enable electrical stimulation to better reach the target muscle and/or nervous tissue. Many variations utilized mechanical methods (e.g., as provided in FIG. 2) to reduce local edema. Other variations and embodiments use alternate techniques to achieve this goal.

The stimulation assembly is shown being applied to a leg of a subject, such as on the thigh or the quadriceps. In other implementations, a stimulation pad may be placed at another location on a subject. For example, a stimulation pad may be used to stimulate other leg muscles, or muscle and/or nervous tissue provided in a subject's arms or torso. For example, the pad may be placed at the rear of the thigh of a subject, around an entire thigh of the subject, in the front of back of the lower leg of the subject, at the upper arm of a subject, at the lower arm of a subject, at the waist of a subject, at the upper torso of a subject, or below the waist of a subject.

A pad and/or assembly producing the desired amount of pressure to remove at least some excess third space fluid may be a tissue fluid displacing pressure pad. The tissue fluid displacing pressure pad and fastener may provide a compressive force to a target muscle and/or nervous tissue, so that at least some excess third space fluid flows away from a tissue region covered by the tissue fluid displacing pad and away from the target muscle and/or nervous tissue.

Figure 3:
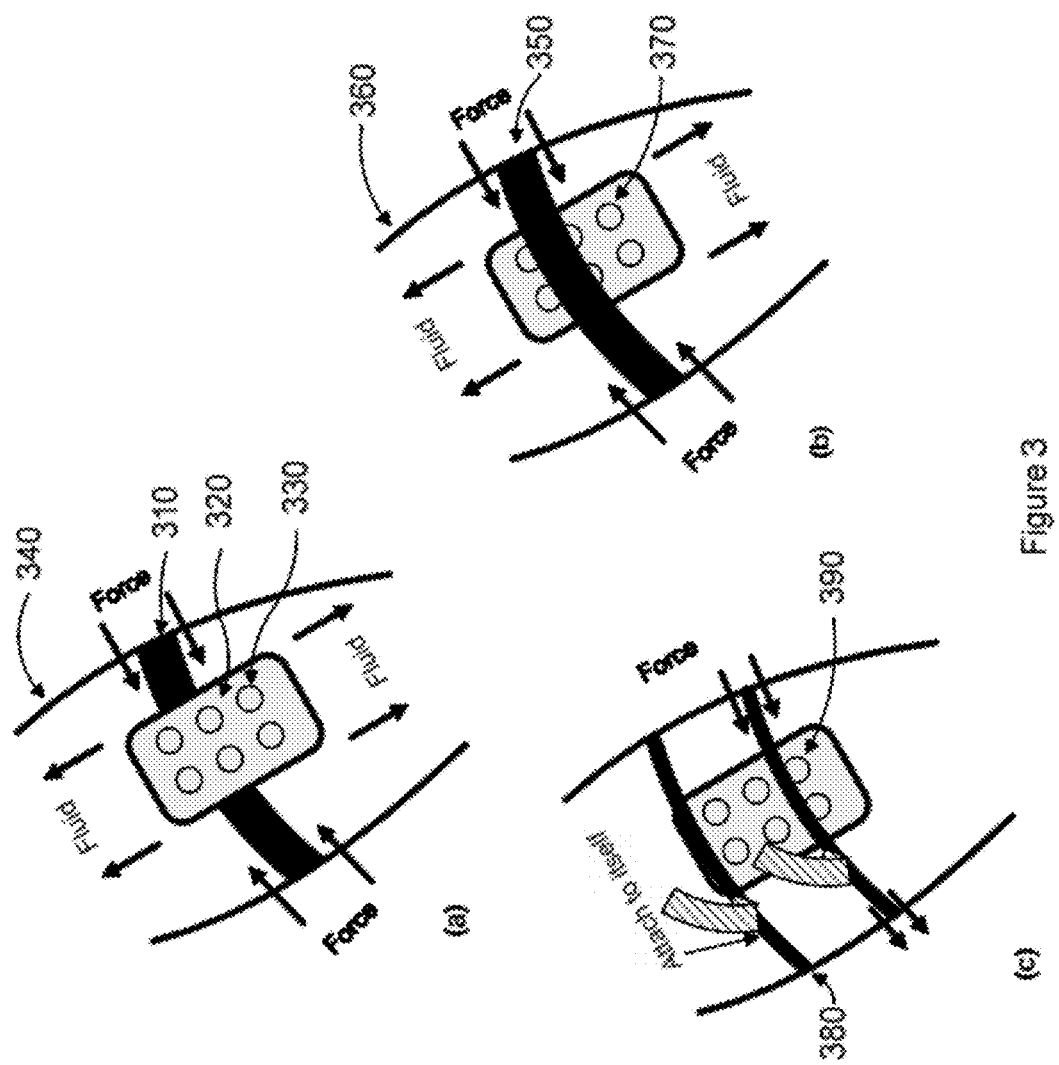
FIGS. 3(*a*)-(*c*) illustrate variations of a stimulation pad involving strap attachment mechanisms.

FIG. 3 illustrates several possible variations of a specialized stimulation pad that involve the use of strap(s) as an attachment mechanism. One embodiment involves the use of a circumferential strap(s) that attaches the pad to the person receiving NMES in the region of desired stimulation. In this variation, if two straps are used, the straps may attach to one another (ex. through a Velcro or hook/clip mechanism) or may attach directly to the pad itself. Alternatively, if a single strap is used it may attach to itself or directly to the pad itself. The strap(s) may be used to secure the stimulation pad firmly to the region of stimulation, ensuring quality contact and helping to achieve good electrical coupling between the skin and electrode. Tightening the strap(s) further will apply pressure to the stimulation region and reduce third space fluid locally. In other embodiments, any type of fastener may be used to secure the stimulation pad.

In FIG. 3(a), a wide strap 310 may originate from each side of the pad 320. The pad may have one or more electrode 330. Alternatively, the strap may be provided on the underside of the pad and may be integrally connected to the pad. The strap may circumscribe a body part 340 of the subject, such as a part of a leg, arm, or torso. Once pulled sufficiently tight to apply a pressure, the straps may be held in place by attaching to one another on the underside of the body part (attachment not shown). The strap may provide a squeezing force around the body part of the subject. This may cause excess third space fluid to leave the region being squeezed.

In FIG. 3(b), one or more straps 350 traverse the circumference of the body part 360 intended to treat with NMES. Once pulled sufficiently tight to apply a pressure, the strap may attach to itself using a fastener such as Velcro, a hook, a button, a clasp, or other mechanism. The strap does not necessarily attach to the stimulation pad 370 directly. In some instances, one or more strap may be an integral part of the stimulation pad that is attached to the stimulation pad, while in other instances, the strap need not be an integral part of the stimulation pad and may lie over the stimulation pad to keep it in place. The one or more straps may provide a squeezing force around the body part of the subject, which may cause excess third space fluid to leave the region being squeezed.

In FIG. 3(c), one or more straps 380 are attached to one side of the stimulation pad 390. Each strap wraps entirely around the body part intended to treat with NMES. Once pulled tight, the strap may be held in place by attaching to itself with a Velcro, hook, button, clasp or other suitable mechanism. In some embodiments, the pad does not circumscribe the body part that it is attached to. For example, a fastener may be used to circumscribe the body part. In other embodiments, the pad itself may circumscribe the body part that it is attached to.

Figure 4:
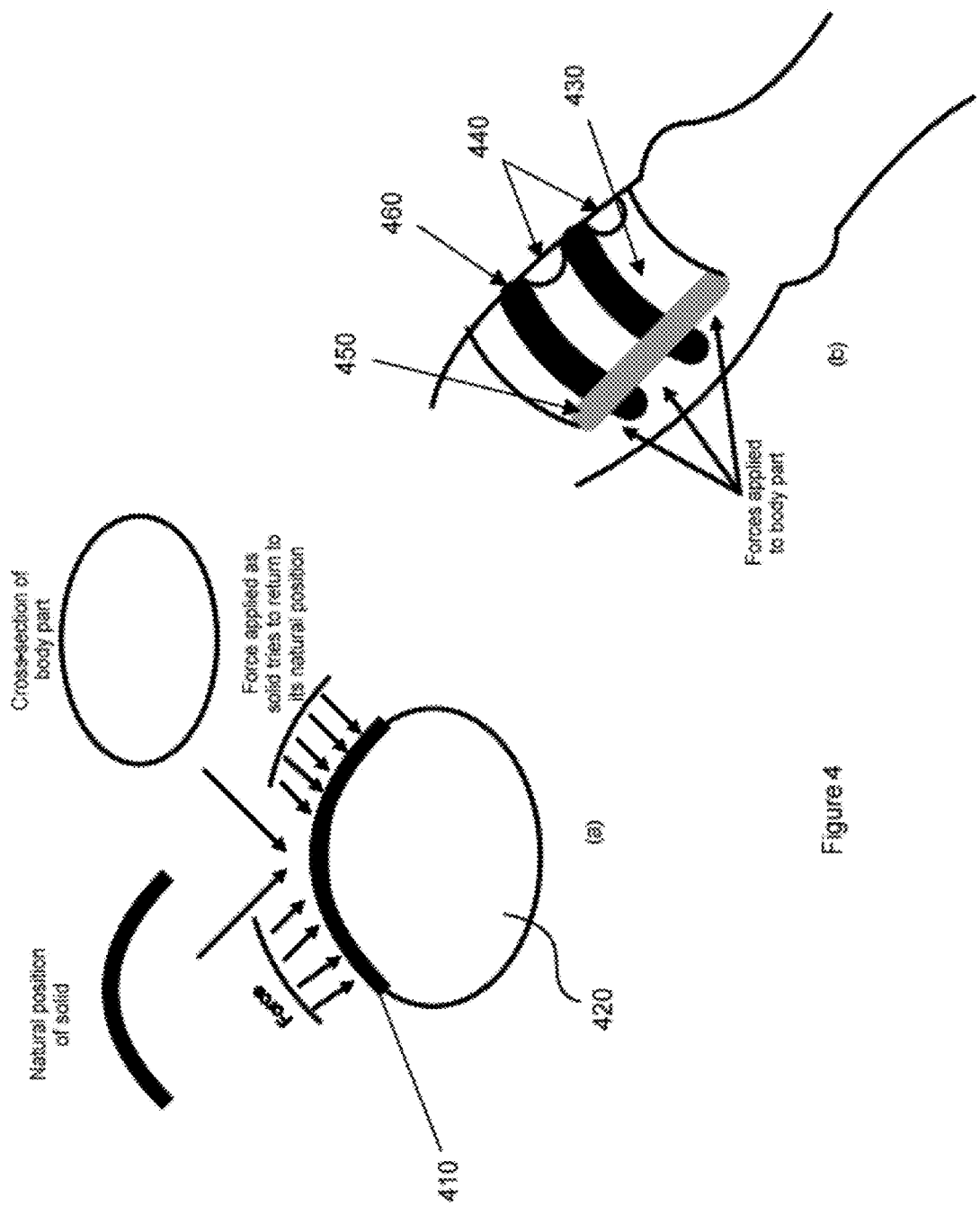
FIGS. 4(*a*) and (*b*) illustrate other embodiments of a stimulation pad including a curved solid component.

FIG. 4 illustrates another embodiment of a stimulation pad including another pressure generating mechanism. The stimulation pad may include a curved solid component. The curved solid component may be flexible and may have a steady state radius of curvature smaller than the body part intended to treat with NMES. For example, if the body part to be treated is a leg, the curved solid component may have a radius of curvature smaller than the radius of the leg, so that it may exert a squeezing force on the leg. The curved solid component may be a solid stretched around the body part.

In accordance with one embodiment, FIG. 4(a) shows a mechanism of action of the flexible solid. In the cross-sectional view, the solid 410 is stretched to a larger radius of curvature to fit over the body part 420 intended to treat with NMES. The restorative forces associated with the solid attempting to reach its steady state radius of curvature may apply a local pressure to the region of stimulation. The local pressure may be sufficient to move at least some excess third space fluid from the region being squeezed. Thus, a tissue fluid displacing curve may provide a compressive force to a target tissue, thereby causing excess third space fluid to flow away from a tissue region covered by the tissue fluid displacing curve, and away from the target tissue.

FIG. 4(b) shows a side view showing a variation of the device and system placed on a person's leg. A stimulation pad 430 may have one or more stimulation electrode 440. The stimulation pad 430 may have insertion slots 450 that allow one or more curved solid components 460 to interface with and be secured to the pad. After the solid component is secured, the pad will retain the shape of the curved shape of the solid component. The stimulation pad may then be placed onto a person's body, stretching the solid component into a larger radius of curvature than its initial position. The solid component may thus exert a constant force on the body part, securing the pad while simultaneously creating a pressure gradient that will move third space fluid out of the region.

Any number of curved solid components may be used. For example, one, two, three, four, or more curved components may be secured to a stimulation pad. The solid components may be arranged to be substantially parallel to one another. Alternatively, the solid components need not be parallel to one another, but may be arranged in such a way to provide the desired amount of pressure to the body part and to conform to the body part. In some instances, if the area covered by a stimulation pad is sufficiently large, and the underlying body part varies is radius or shape, the solid components may have slightly different sizes and/or curvatures to conform to the underlying body part. Also, the solid components may also vary in size and/or curvature to apply different amounts of pressure to the underlying body part. For instance, in some situations, it may be beneficial to apply more pressure to a particular portion of a body part, while another portion of the body part may require less pressure.

In some embodiments, a tissue fluid displacing curve does not have an opposing side. Thus, the fluid displacing curve need not circumscribe an entire body part. The curve may stay on the desired body part by its own squeezing action. In alternate embodiments, additional straps or fasteners may be used to assist with keeping the curve in place.

Figure 5:
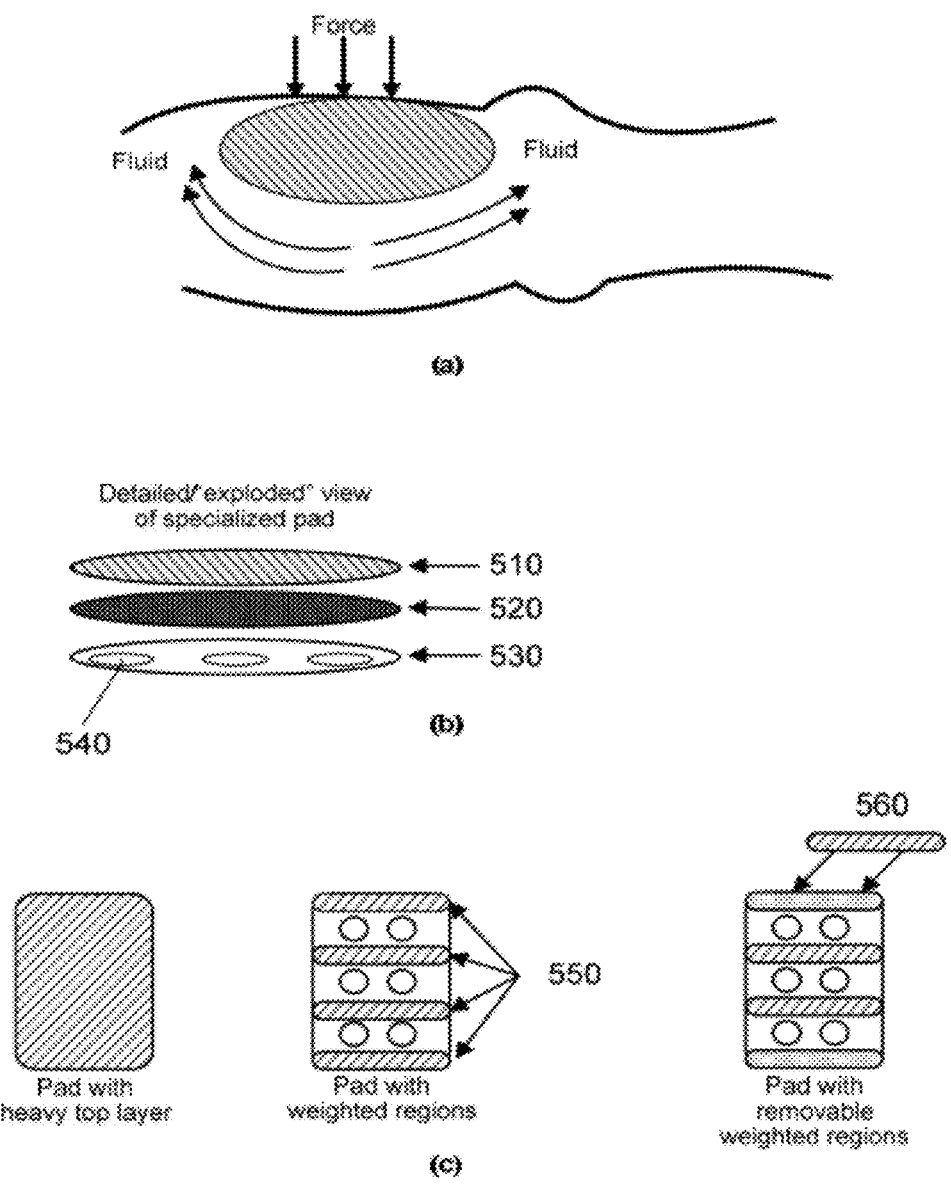
FIGS. 5(*a*)-(*c*) show variations of a stimulation pad involving the use of weighted components.

FIG. 5 shows a variation of a stimulation pad involving the use of another pressure generating assembly. The pressure generating assembly may include weighted components. The weighted components may be integral to the pad, or somehow connected to the pad. Thus, the weighted components may somehow be internal to a pad. In FIG. 5(a), the general mechanism of action is summarized. As shown, force from a relatively heavy pad may create a pressure gradient that can cause excess third space fluid to move away from the intended stimulation site.

FIG. 5(b) shows an 'exploded' view of one variation of the weighted stimulation pad containing three layers: a weighted top layer 510, a middle layer 520 containing pad electronics, cushioning, and other components, and a bottom layer 530 intended for contact with the skin surface containing the stimulation electrodes 540, coupling gel, and potentially an adhesive. Although the various layers are shown in a particular order, the order of layers may be varied. Similarly, the various components described in each layer may also be moved to another layer.

FIG. 5(c) illustrates several potential variations: a pad with a single heavy top layer, a pad with discrete weighted regions built into the main pad body, and a pad with removable/replaceable weighted regions. For example, in one variation, discrete weights 550 or a removable weighted top layer can be optionally applied to the stimulation pad. Removable weights 560 may be attached and/or detached by any mechanism known in the art. For example, the weights may velcro onto a layer, may slip into a pocket designed for the weight, may be magnetically attached, may snap in with a fastener, may hook into place, may be tied into place, or any other fastening technique. Alternatively, a weighted layer or discrete weights can be permanently built into the stimulation pad.

Any number of weights may be provided. For example, a weighted layer may include one, two, three, four, five, six, seven, eight, ten, twelve, or more weights. Including more weights may allow for more variation in weight distribution to provide a desired pressure at a desired region. The weights may or may not be positioned over one or more stimulating or sensing electrode. For example, a weight may be positioned to cover an electrode. Alternatively, the weight may be positioned in proximity to an electrode, but not covering the electrode.

Weights could be comprised of flexible or rigid solid, a liquid, or a solution mixture. It will be apparent to those skilled in the art that many possible materials are available to add significant weight to the stimulation pad. The amount of weight added or built into the pad may be large enough to apply the amount of constant pressure required to remove excess fluid from the stimulation region, but not large enough to collapse vessels or induce other unwanted events. The weight of the pad may also serve to ensure good electrical contact between electrodes in the pad and the surface of the skin.

Any amount of weight may be provided to generate a desired pressure at the desired region. In some instances, a desirable amount of weight may fall in the range of 2-20 lbs, 5-15 lbs, 7-12 lbs. For example, the total of the weights provided may be about 2 lbs, 3 lbs, 5 lbs, 7 lbs, 10 lbs, 12 lbs, 13 lbs, 15 lbs, 17 lbs, 20 lbs, 25 lbs, or 30 lbs.

Figure 6:
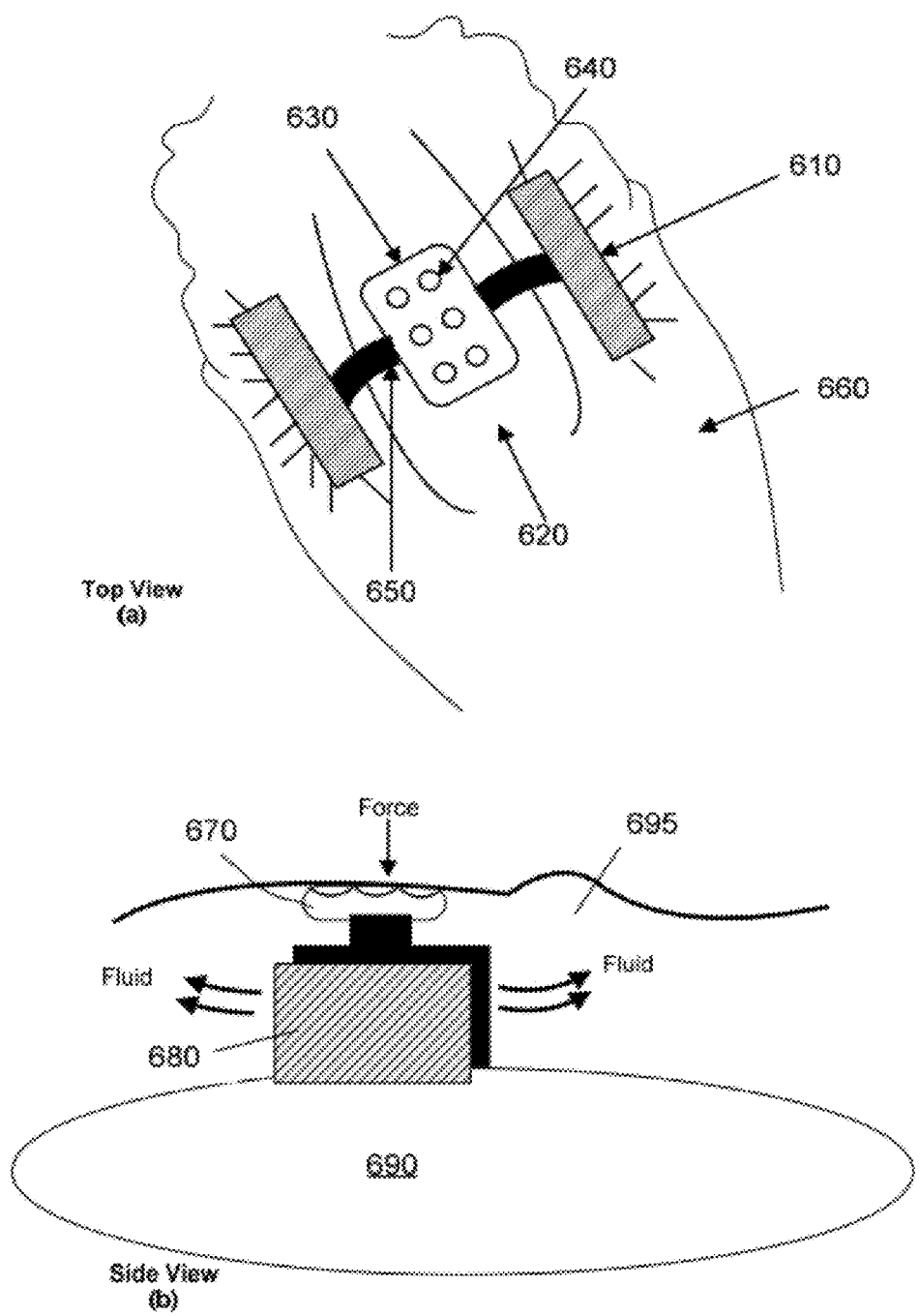
FIGS. 6(*a*) and (*b*) show additional variations of a stimulation pad involving weighted components external to the stimulation pad.

FIG. 6 provides another variation of a stimulation pad that involves the use of weighted components. In some embodiments, the weighted components may be external to the pad. FIG. 6(a) shows a weighted block 610 with attachment slots that may be placed on either side of a person's leg 620 or other body part. The stimulation pad 630, which may have one or more electrodes 640, may be secured to the blocks with a strap 650 or similar mechanism. The mass of the blocks allows for the strap to be pulled sufficiently tight to generate a pressure gradient capable of removing third space fluid from the intended region of stimulation. In some embodiments, the weighted blocks may be placed on top of a bed 660, or other surface that the body part may be resting on.

FIG. 6(b) provides a side view along with the direction of the force produced by adjusting for a tight strap connection between the stimulation pad 670 and the weighted block component 680. The force may be exerted downward on the body part, which may cause at least some excess third space fluid to leave that region.

These embodiments may prove to be particularly useful if NMES were applied to leg muscles. In this situation, weighted supporting components could be placed on top of a bed or chair (or other support surface 690 that holds a person receiving NMES) on either side of the leg(s) 695. These supporting components would be heavy enough to stay in place on the support surface but light enough for an average person to move them without a significant effort, likely on the order of 15-20 lbs, 12-25 lbs, or 10-30 lbs. Straps or other securement mechanisms connected to the stimulation pad are used to attach the pad to the supporting components. In a preferable embodiment, the attachment mechanism may involve a slit or hole that a strap can be inserted through. Taking advantage of the weight of the supporting component, the straps may be adjusted to hold the pad tightly to the skin. Pressure from the pad can create good electrical contact between skin and electrodes and also remove excess fluid from the stimulation region. An additional benefit of this variation is that supporting components may hold a person's legs safely in place during NMES therapy.

Figure 7:
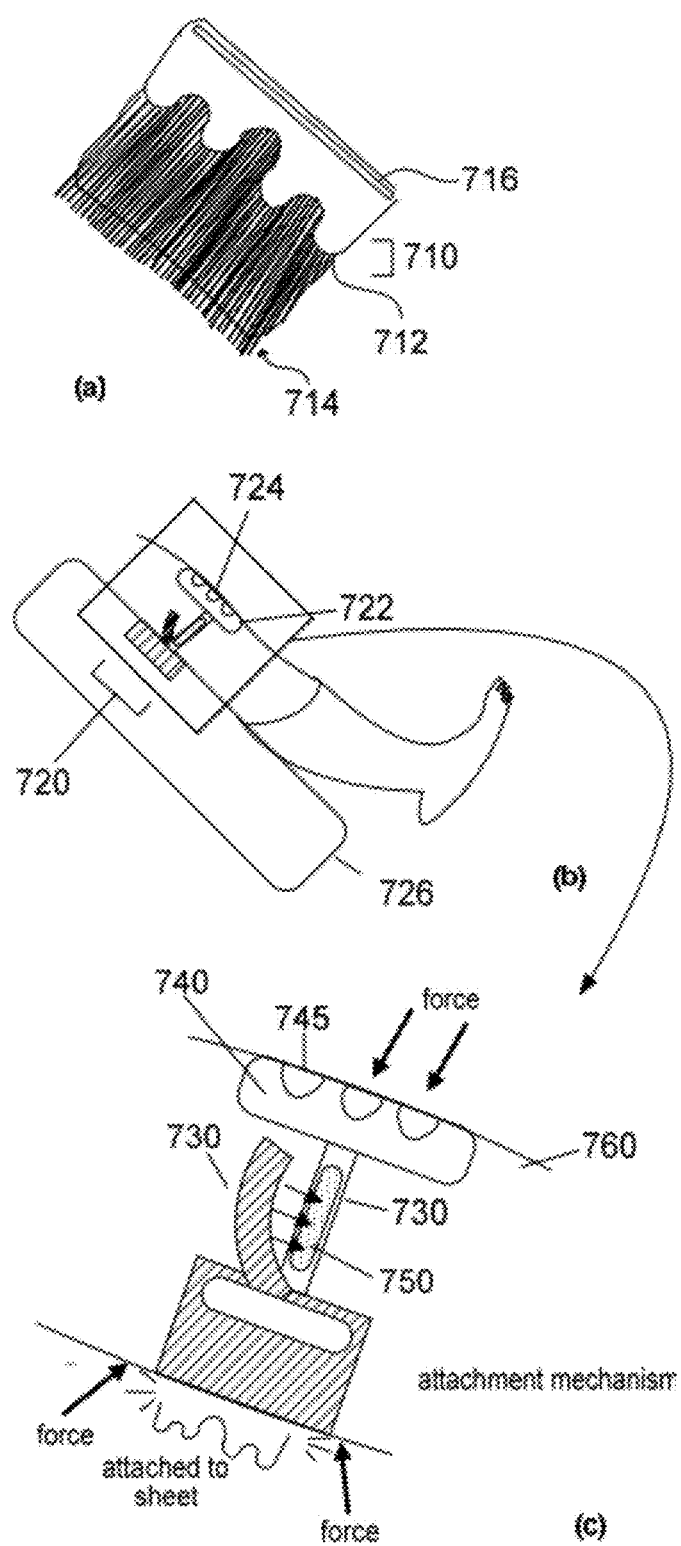
FIGS. 7(*a*)-(*c*) show a stimulation pad with a direct attachment to a bed or support surface.

FIG. 7 shows a stimulation pad with a direct attachment to a bed or support surface. A support surface may be any surface providing support to a body part utilizing the stimulation pad. The support surface can be a bed, desk, chair, counter, or any type of loose-fitting support surface. This configuration may be especially useful if the person receiving NMES is positioned on a bed or another surface with a fairly loose-fitting exterior (for example, a bed sheet) or features that may readily accept a connection (e.g., loops, protrusions, bars, etc.).

FIG. 7(a) provides one variation of the attachment mechanism. A clip 710 with rounded edges 712 may be used so that a strong grip on a sheet 714 can be achieved without tearing or damaging it. The clip may have an insertion slot 716 to interface with a strap or other mechanism connected to or circumventing the stimulation pad. The clip may have any other attachment mechanism that may allow the clip to be connected to some mechanism that assist with holding the stimulation pad in place, such as holes to accept a connector, snap fittings, lock and groove fittings, screw fittings, hooked fittings, elastic tension fittings, belt type fittings, and so forth.

A clip (or other suitable mechanism) may be used to attach to the covering surface on either side of the body part (ex. leg) intended to treat with NMES. Thus, in some embodiments, two clips may be provided (e.g., one on each side of a body part). Alternatively, only one clip may be needed to attach to a surface. In some instances, additional clips or attachment mechanisms may be provided so that three, four, five, six, or more attachment mechanisms may assist with securing the stimulation pad to the body part and the support surface.

FIG. 7(b) shows a side view showing the attachment mechanism 720 and strap affixing a stimulation pad 722 to a person's leg. The stimulation pad may have one or more stimulation electrode 724. A subject's body part, such as a leg, may be resting on a support surface, such as a bed 726. A stimulation pad, comprising stimulation electrodes, may be contacting the body part. An attachment mechanism may be provided that may connect the stimulation pad with the support surface. The connection may be strong enough to generate a sufficient pressure to cause at least some excess third space fluid to be moved away from the target tissue for stimulation.

As previously mentioned, the attachment mechanism may be a clip that can grasp onto the support surface and connect to a strap from the stimulation pad. However, any other attachment mechanism may be used. In some embodiments, the support surface itself may have features that may allow the stimulation pad to be attached to the support surface. For example, a bed may have loops or bars through which straps from a stimulation pad may be tied down or otherwise connected.

FIG. 7(c) a detailed view of an attachment mechanism. A strap 730 may originate from each side of the stimulation pad 740 (which may have an electrode 745), inserts through the slit in a clip, and once pulled tight can hold its position by attaching to itself. In some instances, it may attach to itself using Velcro 750, may be tied to itself, or may have some fastener connecting it to itself. Thus, in some embodiments, strap(s) (with or without Velcro) or another suitable mechanism that will be apparent to those skilled in the art will be placed through or around securement ports in the clips/attachment mechanism. Tightly-pulled straps may apply force both to the top of the body part 760 (via the stimulation pad) and to the bottom portion of the body part (through the sheet/support structure). The strap(s) could be attached to the stimulation pad, traverse the face of the stimulation pad, or interface with the pad in another way that allows them to apply pressure on the pad in the direction of the body part receiving NMES. Complementing the pressure from the strap(s) could be additional pressure produced by the covering surface as the straps pull it in tension across the underside of the body part receiving therapy.

The result may be a local pressure gradient that will move third-space fluid outside of the region of treatment. Advantages of this variation may include the fact that pressure can be applied around the complete circumference of the body part receiving therapy, increasing the effectiveness of fluid removal. An additional advantage is that circumferential pressure and full circumference stimulation pad attachment can be accomplished without having to move the person (for example, lift a heavy limb such as a leg). This second advantage would be particularly useful to medical care providers applying NMES to sedated or comatose persons. An embodiment somehow attaching the pad to a support surface, or an embodiment utilizing weight may preferably used for an immobile individual.

Figure 8:
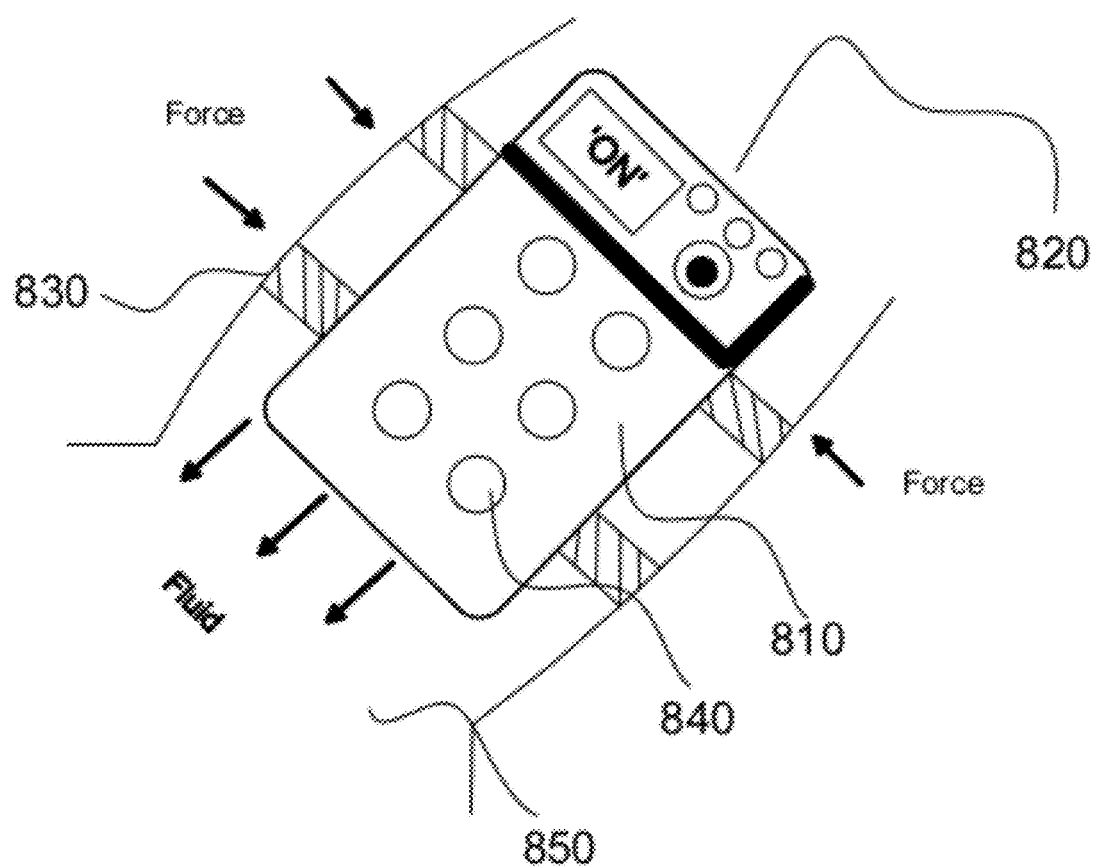
FIG. 8 provides an embodiment of the system with a control unit and a stimulation pad constructed as a single unit.

FIG. 8 shows an embodiment where the stimulation pad 810 and the control unit 820 are comprised of a single unit. The pad and control unit may be mechanically connected. The pad and control unit can be integral so that the control unit is built directly into the stimulation pad. In the variation shown, straps 830 are used to apply pressure locally, removing excess third space fluid from the region. However, it will be clear to those skilled in the art that any of the variations of producing a local pressure gradient that are described herein may also be compatible with the integrated stimulation pad and control unit.

In the example shown, the stimulation pad 810 may have a stimulation electrode 840 and be in contact with the control unit 820. One or more straps 830 may be provided, thereby exerting a compressive force on a body part 850 circumscribed by the strap. This may cause at least some fluid to leave the region that is being stimulated.

Figure 9:
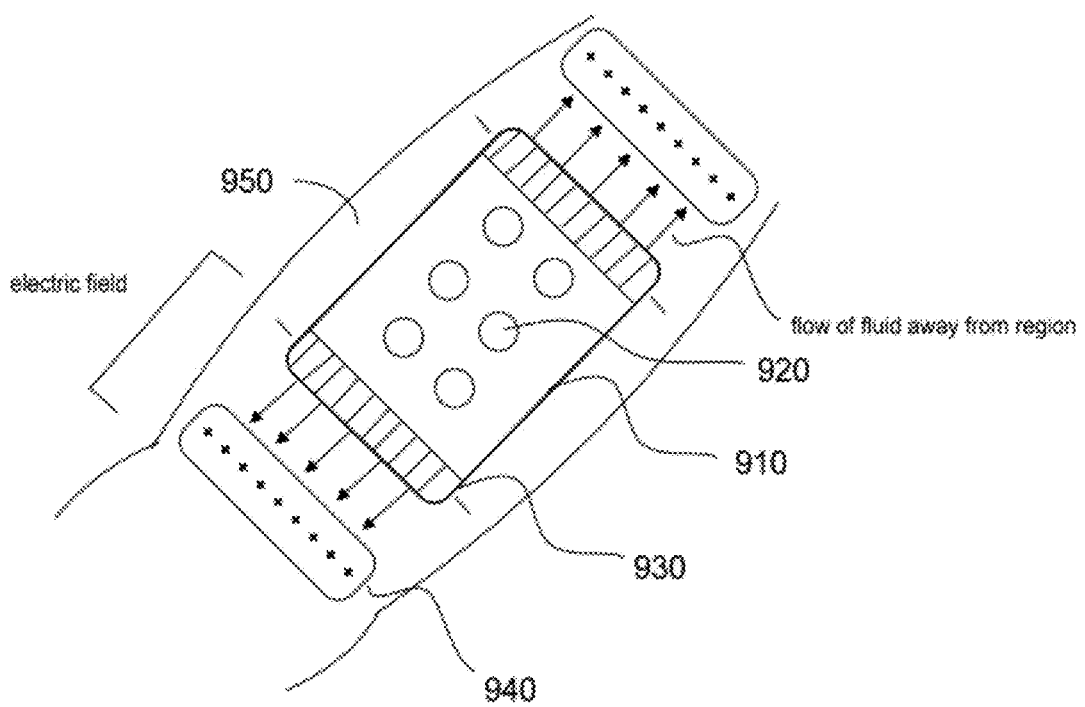
FIG. 9 provides an embodiment of the system that utilizes local electrical field gradients.

FIG. 9 shows an embodiment of the NMES system that utilizes local electric field gradients. The NMES system may involve the use of electric fields on either side of the stimulation pad 910. The stimulation pad may have a plurality of stimulation electrodes 920. The edges of the stimulation pad may be charged and may use polarized electrodes 930. Electrodes 940 that are polarized with the opposite charge may be placed nearby. For example, the edges of the stimulation pad 930 may be negatively charged so that the oppositely polarized electrodes 940 are positively charged. Alternatively, the edges of the stimulation pad may be positively charged so that the oppositely polarized electrodes are negatively charged.

If a limb were the body part 950 receiving NMES therapy, it could be preferable that these electric fields are oriented along the long axis of the limb in question. In this embodiment, the edges of the stimulation pad along the long axis may be given an electrical charge. Thus, in some embodiments, two of the edges of the stimulation pad may be given the electrical charge. In other embodiments, the body part receiving the NMES may not be limb (e.g., may be part of the torso, etc.). It may be preferable in some cases that the fields be oriented in all directions from the pad. In some situations, all of the edges of the stimulation pad may be given the electrical charge.

The oppositely charged electrodes may be attached onto or near the skin surface a short distance away from the stimulation pad. The oppositely charged electrodes may be attached using adhesives, straps, or another suitable attachment mechanism. In some embodiments, the electrodes may be part of an oppositely charged electrode pad (which may include a substrate, such as a flexible housing), or may be individually placed at the desired locations. The resulting electrical field may move charged particles, as well as excess third space fluid, away from the region of stimulation. The presence of the electrical field gradient may draw charged particles in third space fluid away from the region of stimulation. Excess water will also be drawn out of the region naturally as the body attempts to maintain local isotonic conditions.

Figure 10:
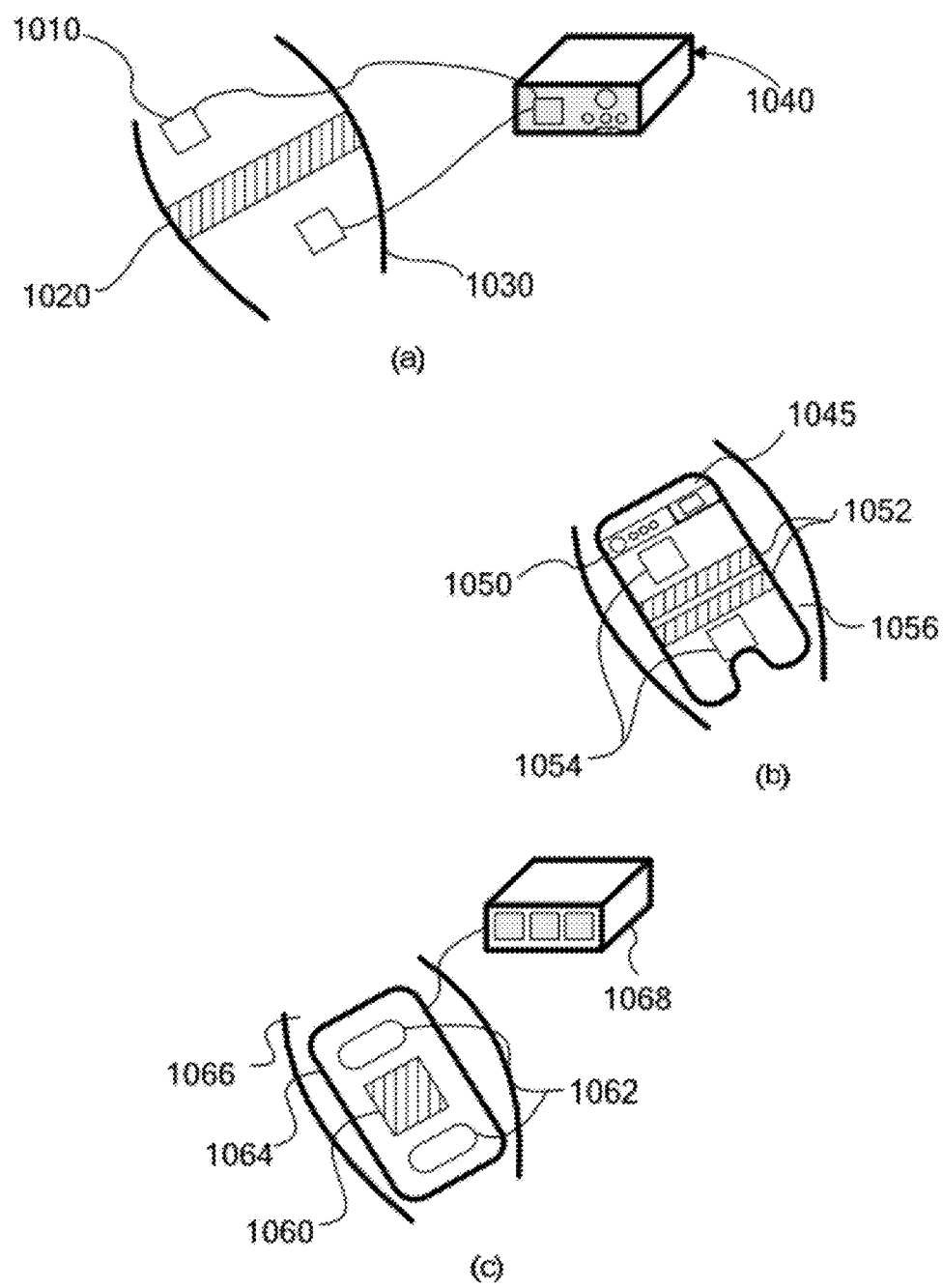
FIGS. 10(*a*)-(*c*) illustrate various embodiments where pressure gradients are applied in selected locations.

FIG. 10 illustrates an NMES system where pressure gradients may be applied in selected locations. Pressure may be applied to tissues in specific regions to reduce local edema and improve NMES performance. The region where pressure is applied to tissue may or may not correspond with the region(s) where stimulation electrodes make contact with the skin. The representations provided in FIG. 10 serve only as examples, and those skilled in the art will recognize that other potential implementations exist.

FIG. 10(a) shows one embodiment that uses discrete and spatially-independent electrodes 1010 instead of a stimulation pad. A pressure generating mechanism 1020 may be located at a desired location to apply local pressure. The electrodes and the pressure generating mechanism may be placed on a body part 1030. A control unit 1040 may control signals to the electrodes and/or pressure generating mechanism. Thus, a pressure generating mechanism (any or all of the previously described mechanisms may be used) may sit strategically in the region of stimulation to reduce local edema. In some embodiments, the desired location may be in the tissue region between two or more electrodes. In other embodiments, the pressure generating mechanism may be applied between electrodes, outside electrodes, in a region encompassing the electrodes, or in another suitable manner. In some instances, the pressure generating mechanism may be placed at a predetermined distance from one or more electrodes. Similarly, the electrodes may be placed at a pre-calculated location relative to the pressure generating mechanism. The relative positions of the electrodes and pressure mechanism may enable the stimulation to be provided at a desired location relative to the reduced local edema. Having the electrodes as discrete from the pressure generating mechanism may provide flexibility in electrode placement, which may provide a more universal set of components that can be applied to various subjects and/or body parts.

In a further variation, it may be advantageous to apply pressure only to certain sub-regions in the region of stimulation. In an example embodiment, a weight or other pressure generating mechanism may be placed between stimulation electrodes (with or without the use of a stimulation pad) in a manner such that pressure is exerted with a transverse footprint less wide than the transverse span of the electrode region.

FIG. 10(b) shows a stimulation pad 1045 with a built-in control unit 1050 using one or pressure generating mechanisms 1052 in the location between the stimulation electrodes 1054 to create a pressure gradient. A substrate of the stimulation pad may assist with providing a relative distance between the stimulation electrodes and the pressure generating mechanism. For example, if a fixed distance or relative position is desired between the electrodes and pressure generating mechanism, the pad may allow repetition of placement. The stimulation pad may be placed on a body part 1056 being stimulated.

In some embodiments, one, two, three, or more pressure generating mechanisms may be provided. In some instances, various amounts of pressure may be desired at various locations. As previously mentioned, these locations may be between electrodes, outside electrodes, adjacent to electrodes, or in some desired proximity to a stimulating electrode. A pressure generating mechanism does not have to be in the region of a stimulating electrode. The pressure generating mechanism may be provided to move underlying excess third space fluid, and does not have to be over, in contact with, or in the same region as the stimulating electrode to do so.

FIG. 10(c) shows a pressure generating mechanism 1060 that is located in the tissue region between NMES stimulation electrodes 1062, with the transverse footprint of the pressure generating mechanism smaller than the transverse span of the stimulation electrodes. In some embodiments, it may be desirable for the pressure generating mechanism to be less wide than the transverse span of the stimulating electrodes. For example, it may be beneficial for the pressure generating mechanism to be 97% as wide, 95% as wide, 90% as wide, 85% as wide, 80% as wide, 70% as wide, 50% as wide, or be at any width relative to the stimulating electrode spans. In alternate embodiments, the pressure generating mechanism may be wider than the transverse span of stimulating electrodes.

The stimulation electrodes 1062 and/or the pressure generating mechanism 1060 may be on a stimulation pad 1064. The stimulation pad may be resting on or somehow attached to a body part 1066 receiving NMES. A control unit 1068 may be in communication with one or more parts of the stimulation pad.

Figure 11:
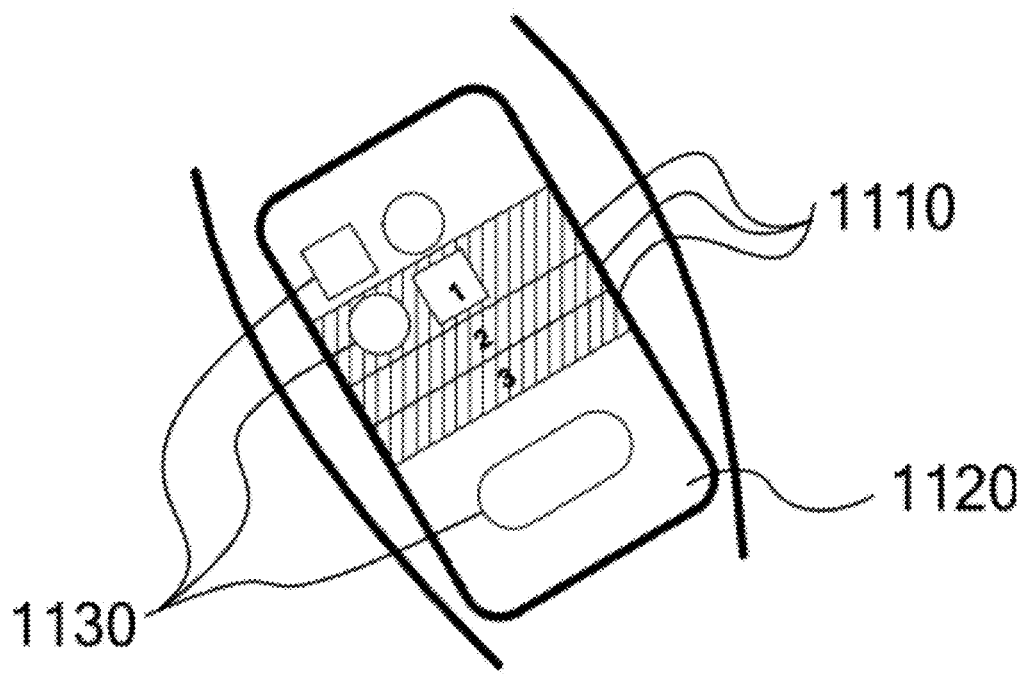
FIG. 11 shows an embodiment where a plurality of pressure generation zones may be provided.

FIG. 11 shows an NMES assembly that may utilize two or more zones of pressure generation. For example, two, three, four, five, six, or more zones of pressure generation may be provided. As shown, three discrete pressure generating mechanisms 1110 for three zones of pressure may be built-in or used in conjunction with a stimulation pad 1120 for NMES. Each zone (labeled 1, 2, and 3 in FIG. 11) may exert the same or different amounts of pressure on local tissues. Thus, different amounts of pressure may be applied to different regions of tissue in the region of stimulation.

Without wishing to be bound by any theory, it is believed that creating a pressure gradient will allow for fluid in edematous tissue to be locally reduced in a manner where the direction of fluid movement can be at least partially controlled. For example, in some scenarios it may be desirable to shift the location of third space fluid in a particular manner such that NMES performance is improved as much as possible. To provide one example implementation, three adjacent zones of pressure may be created by placing weights of three different masses adjacent to one another. In this example, the weights are arranged such that the most massive weight and least massive weights are not next to one another. A pressure gradient may be created by the weights, partially forcing excessive tissue fluid away from the zone of stimulation. This principle may be generalized so that when multiple zones of pressure are created, the compression components generating the pressure may be arranged to create a pressure gradient. The pressure gradient may be such that the compression component providing the most force is not adjacent to the compression component providing the least force. In some instances, the adjacent compression components may be arranged in order going from the least force to the most force, or vice versa.

The NMES assembly may include one or more stimulation electrode 1130. The stimulation electrodes may have any placement, shape, configuration, or size. The stimulation electrodes may or may not be covered by a compression component (e.g., 1110). In some embodiments, some stimulation electrodes may be covered by a compression component while some may not.

The pressure exerted by each zone may be static through time or may vary based upon input from the NMES operator, a control unit, another mechanism, or some combination of mechanisms. For example, variance of the pressure exerted may occur manually. For example, over time an operator may add more weights, or tighten or loosen more straps to increase or decrease the pressure. Variance of pressure over time may also occur automatically. For example, a mechanism may be provided that may automatically tighten or loosen straps, or inflate or deflate components, or somehow otherwise vary the pressure without requiring human intervention. In some embodiments, variance of the amount of pressure may be controlled by a control unit. The control unit may receive measurements from one or more sensor and may adjust the pressure accordingly. Alternatively, the control unit may adjust the pressure according to time without requiring any feedback from sensors.

In some embodiments, the location of the pressure may be static or may be varied over time. Similarly, the pressure location may be based on input from the NMES operator, a control unit, another mechanism, or some combination of mechanisms. Variance of the pressure location(s) may occur manually. For example, over time an operator may move weights around, or adjust the location of straps to vary the pressure location. Variance of pressure over time may also occur automatically. For example, a mechanism may be provided that may automatically move straps, or inflate or deflate different components, or somehow otherwise vary the pressure location without requiring human intervention. In some embodiments, variance of the location of pressure may be controlled by a control unit. The control unit may receive measurements from one or more sensor and may adjust the pressure location accordingly. Alternatively, the control unit may adjust the pressure location according to time without requiring any feedback from sensors.

Any combination of automatic readjustment and human intervention may be utilized. Any variance may be controlled automatically via a compression control mechanism that may be capable of varying the amount and/or location of the compressive force. When multiple compression components are provided, they may each be independently controllable.

Figure 12:
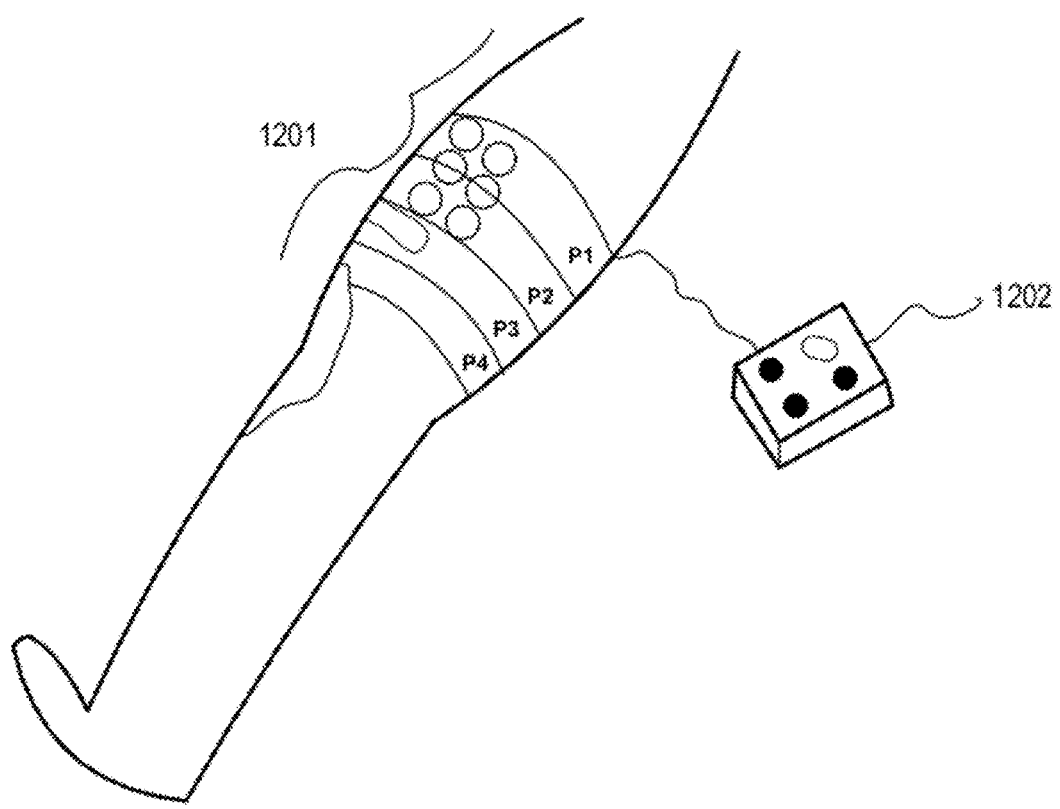
FIG. 12 provides an additional embodiment with a plurality of pressure generation zones.

FIG. 12 provides an additional embodiment with a plurality of pressure generation zones. The stimulation pad (and potentially various sensors) may be integrated into a circumferential sleeve 1201 that may allow for sequential compression of the body part being treated with NMES. As shown, the sleeve has four regions (marked P1-P4), each of which can be applying a different level of pressure to tissues. Although four regions are shown, any number of pressure regions (one, two, three, four, five, six, or more) may be provided. Pressure control may be accomplished through electronics in the control unit 1202.

As mentioned, sequential compression of the body part being treated may be provided. For example, P1 may be squeezed first, then P2 after the pressure in P1 has diminished, and then P3 after the pressure in P2 has diminished, and so forth. The various pressure regions may have their pressure values increased or decreased at any time. For example, in some embodiments, it may be desirable to have P1 and P3 simultaneously squeezed and P2 and P4 simultaneously squeezed. In another example it may be desirable to have P2 and P3 simultaneously squeezed and then P1 and P4 simultaneously squeezed. The various pressure regions may have their pressures controlled in order to allow a desired distribution of underlying third space fluid, or to allow a desired blood flow.

In other embodiments, air cuffs, balloons, or inflatable lumens may be used as the pressure generating mechanism. Air cuffs or balloons may be used alone or in conjunction with another pressure generation mechanism (ex. straps, weights, elastic bodies, etc) to create or enhance a pressure gradient in the region of NMES therapy. A fluid displacing pressure pad may incorporate air cuffs, balloons, and/or inflatable lumens. In one implementation, a strap mechanism may circumscribe the body part receiving NMES, and a velcro, snap, elastic component, hook, or other attachment mechanism may hold the strap in place and with a fixed diameter. The air cuffs or balloons may be filled with air or any other gas, or with water or any other fluid.

The underside (facing body part) of the strap may be fitted with a series of inflatable lumens or balloons which connect to a filling apparatus such as a hand pump, air compressor, or other suitable filling mechanism. A tissue fluid displacing pressure pad may be connected to the filling apparatus to inflate/fill or deflate/empty the pad, thereby varying the compressive force provided by the pad. The strap by itself may be used with lumens uninflated to reduce local tissue edema and improve NMES performance. Further edema reduction may be accomplished by inflating lumens such that additional pressure may be exerted on tissue in the region of stimulation, leading to further NMES performance increases. The degree of inflatedness may be controlled by a control unit, or may be controlled manually by an operator. For example the control unit may control the filling apparatus to provide a desired compressive force to a target muscle and/or nervous tissue. In some instances, the degree of inflatedness may vary over time during an NMES treatment. The implementation described above was provided by way of example, and those skilled in the art will recognize that other implementations and variations of these embodiments are plausible.

As previously discussed, it may be desired to have the degree of pressure exerted on tissue to vary with time. For example, it may be desirable to alternate pressure on and off in one location, or to shift pressure from one location to another one or more times throughout NMES treatment. Alternatively, it may be desirable to change the amount of pressure in one or more locations over time in order to optimize the flow of excessive tissue fluid away from tissue regions where it will impact NMES performance. Variations in pressure could be accomplished manually (ex. through movement or replacement/readjustment of weights, straps, etc) or automatically (ex. inflation/deflation of an air cuff or balloon mechanism).

In a variation of the preferred embodiments, it may be desired to apply pressure to tissue outside of the region of stimulation. This pressure may be stand-alone or may be combined with mechanisms that exert pressure on tissue in the region of stimulation.

The method described herein can be utilized effectively with any of the embodiments or variations described above, as well as with other embodiments and variations not described explicitly in this document. The method includes several steps. In one step, the device and system are interfaced with an edematous person, for example by attaching the specialized stimulation pad in one of the manners described above. In a second step, the device and system are adjusted so that the pressure gradient, electrical field gradient, or other force is sufficient to move excess third space fluid away from the region of stimulation. In a third step, NMES therapy is delivered to the person. In some embodiments, the second and third steps may be repeated, so that the device and systems may be readjusted so that the pressure gradient or other force is readjusted. The NMES therapy may continue between the readjustment steps or during the readjustment. The readjustment may occur in response to signals received by sensors during the NMES therapy.

In some embodiments, a compressive force may be provided prior to providing a stimulation signal to an electrode. The compressive force may be provided for a predetermined amount of time prior to stimulation. The predetermined amount of time may be for any amount of time including but not limited to 15 seconds, 30 seconds, 45 seconds, 1 minute, 90 seconds, 2 minutes, 3 minutes, 4 minutes, 5 minutes, 7 minutes, 10 minutes, 15 minutes, or 20 minutes before stimulation occurs. Providing a compressive force prior to beginning stimulation may allow the desired excess third space fluid to be removed prior to stimulation. This removal may be temporary or relatively permanent. For example, one sequence of events may be that the compressive force is applied for several minutes, then NMES stimulation may occur for 30 minutes, the stimulation assembly and/or pressure assembly may be removed, and fluid may move back into the stimulation area.

In some instances, a method for electrically stimulating a selected stimulation a region of a subject may include placing at least one stimulating electrode in electrical communication with a target muscle and/or nervous tissue of the subject. Optionally, a sensor may be placed to be in electrical communication with the target muscle and/or nervous tissue. A compressive force may be provided to the target muscle and/or nervous tissue of the subject. The compressive force may be within a predetermined pressure range sufficient to move excess third space fluid from a stimulation region proximate to the target muscle and/or nervous tissue. For example, the predetermined pressure range may be within 2-20 lbs for the area of force covered by the compressive force. The method may also include providing an electrical stimulation signal to the stimulating electrode, thereby electrically stimulating the target muscle and/or nervous tissue from which at least some excess third space fluid has been moved. Optionally, a feedback signal from the sensor may be received. In some instances, based on a feedback signal from the sensor, the stimulation signal sent to the stimulation electrode and/or the compressive force provided to the target tissue region may be adjusted or maintained. In some embodiments, a controller may be providing the stimulation signals and receiving any feedback signals. A controller may also be directing the compressive force provided to the target tissue region. For example, the predetermined pressure range may be determined by the controller.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A system for neuromuscular electrical stimulation comprising:
    a stimulation assembly formed of at least one stimulating electrode for providing electrical stimulation to a target muscle and/or nervous tissue;
    a controller in electrical communication with the at least one stimulating electrode, wherein the controller provides a stimulation signal to the at least one stimulating electrode; and
    a tissue fluid displacing pressure pad and fastener for providing a compressive force to the target muscle and/or nervous tissue, wherein the compressive force is within a predetermined pressure range sufficient to move excess third space fluid from a stimulation region proximate to the target muscle and/or nervous tissue.

2. The system of claim 1 wherein the tissue fluid displacing pressure pad incorporates at least one of the following: a weight, a strap, an elastic component, a hook, a snap, or a hook-and-loop fastener.

3. The system of claim 1 wherein the tissue fluid displacing pressure pad and fastener do not circumscribe a body part of a subject receiving stimulation.

4. The system of claim 1 wherein the tissue fluid displacing pressure pad incorporates at least one of the following: an air cuff, a balloon, or an inflatable lumen.

5. The system of claim 4 wherein the tissue fluid displacing pressure pad is connected to a filling apparatus configured to further inflate or deflate the tissue fluid displacing pressure pad, thereby varying the compressive force provided by the tissue fluid displacing pressure pad.

6. The system of claim 5 wherein the controller controls the filling apparatus to provide a desired compressive force to the target muscle and/or nervous tissue.

7. The system of claim 1 wherein the stimulation assembly further comprises at least one sensor for providing a feedback signal indicative of a parameter related to the target muscle and/or nervous tissue and the controller is in electrical communication with the at least one sensor and receives a feedback signal from the at least one sensor.

8. The system of claim 7 wherein the stimulation assembly is formed with a plurality of stimulating electrodes and/or a plurality of sensors.

9. The system of claim 1 wherein the tissue fluid displacing pressure pad is integrally connected to the stimulation assembly.

10. The system of claim 1 wherein the tissue fluid displacing pressure pad is not integrally connected to the stimulation assembly.

11. The system of claim 1 wherein the controller provides an electrical stimulation signal to the at least one stimulating electrode based on the feedback signal.

12. The system of claim 11 wherein the controller provides the electrical stimulation signal by controlling at least one of the following: pulse width, voltage amplitude, current amplitude, waveform shape, pulse frequency, or relative on/off time between repeating series of pulses.

13. The system of claim 1 further comprising an electrical sensor adapted to provide an electrical feedback signal to the controller that is indicative of a parameter related to the target muscle and/or nervous tissue, wherein the controller is adapted to modify the compressive force based on the electrical feedback signal.

14. A method for electrically stimulating a selected stimulation region of a subject comprising:
    placing at least one stimulating electrode in electrical communication with a target muscle and/or nervous tissue of the subject;
    providing a compressive force to the target muscle and/or nervous tissue of the subject, wherein the compressive force is within a predetermined pressure range sufficient to move excess third space fluid from a stimulation region proximate to the target muscle and/or nervous tissue; and
    providing an electrical stimulation signal to the at least one stimulating electrode, thereby electrically stimulating the target muscle and/or nervous tissue from which excess third space fluid has been moved.

15. The method of claim 14 further comprising:
    placing at least one sensor in electrical communication with the target muscle and/or nervous tissue of the subject; and
    receiving a feedback signal from the at least one sensor.

16. The method of claim 15 wherein the electrical stimulation signal is provided by a control unit and the feedback signal is received by the control unit.

17. The method of claim 16 wherein the predetermined pressure range is determined by the control unit.

18. The method of claim 17 wherein the predetermined pressure range is within 2-20 lbs for the area covered by the compressive force.

19. The method of claim 14 wherein the target muscle and/or nervous tissue of the subject is edematous.

20. The method of claim 14 wherein the compressive force is provided over the location of the stimulating electrode.

21. The method of claim 14 wherein the compressive force is provided in proximity to, but not over, the location of the stimulating electrode.

22. The method of claim 14 wherein the compressive force is applied for a predetermined period of time before stimulation occurs.

23. The method of claim 14 wherein the compressive force is applied for at least 5 minutes.

24. The method of claim 14 wherein the compressive force is provided with a transverse footprint less than the width of the transverse span provided by the at least one stimulating electrode.

25. The method of claim 14 wherein the amount and/or location of the compressive force is varied with time.

26. The method of claim 25 wherein the variance is controlled manually.

27. The method of claim 25 wherein the variance is controlled automatically via a compression control mechanism that is capable of varying the amount and/or location of compressive force.

28. The method of claim 14 further comprising receiving an electrical feedback signal from an electrical sensor in response to the electrical stimulation signal, the feedback signal indicative of a parameter related to the target muscle and/or nervous tissue, and modifying the compressive force based on the electrical feedback signal.

29. A system for electrical stimulation of muscle and/or nervous tissue comprising:
    at least one stimulating electrode for providing electrical stimulation to a target muscle and/or nervous tissue;
    a controller in electrical communication with the at least one stimulating electrode, wherein the control unit provides a stimulation signal to the at least one stimulating electrode; and
    a pressure assembly comprising a plurality of compression components, wherein each compression component provides a force to a different region proximate to the target muscle and/or nervous tissue, and wherein at least two compression components are independently capable of providing a different amount of force.

30. The system of claim 29 wherein the stimulating electrode is provided within a stimulation pad with a substrate.

31. The system of claim 30 wherein the pressure assembly is integrally mechanically coupled to the stimulation pad.

32. The system of claim 30 wherein the substrate is a thin flexible covering.

33. The system of claim 29 wherein the compression components are arranged to create a pressure gradient such that the compression component providing the most force is not adjacent to the compression component providing the least force.

34. The system of claim 29 wherein such force is sufficient to move excess third fluid space from the region.

35. A system for neuromuscular electrical stimulation comprising:
    a stimulation assembly formed of at least one stimulating electrode for providing electrical stimulation to a target muscle and/or nervous tissue;
    a controller in electrical communication with the at least one stimulating electrode, wherein the controller provides a stimulation signal to the at least one stimulating electrode; and
    a tissue fluid displacing curved component for providing a compressive force to the target muscle and/or nervous tissue, wherein the tissue fluid displacing curved component incorporates a rigid or semi-rigid body with a steady state radius of curvature smaller than a subject body part associated with the target muscle and/or nervous tissue.

36. The system of claim 35 wherein the tissue fluid displacing curve does not have an opposing side.

37. The system of claim 35 wherein the tissue fluid displacing curve thereby causes excess third space fluid to flow away from a tissue region covered by the tissue fluid displacing curve and away from the target muscle and/or nervous tissue.

* * * * *